United States Patent
Valbin et al.

(10) Patent No.: US 9,559,290 B2
(45) Date of Patent: Jan. 31, 2017

(54) METHOD FOR PRODUCING A FLEXIBLE PIEZOELECTRIC SENSOR

(71) Applicants: CHAMBRE DE COMMERCE ET D'INDUSTRIE DE REGION PARIS ILE DE FRANCE, Paris (FR); BODYCAP, Caen (FR)

(72) Inventors: Laurie Valbin, Chelles (FR); Lionel Rousseau, Le Perreux sur Marne (FR); Fabrice Verjus, Creully (FR)

(73) Assignees: CHAMBRE DE COMMERCE ET D'INDUSTRIE DE REGION PARIS ILE DE FRANCE, Paris (FR); BODY CAP, Heouville Saint Clair (FR)

( * ) Notice: Subject to any disclaimer, the term of this patent is extended or adjusted under 35 U.S.C. 154(b) by 0 days.

(21) Appl. No.: 14/893,212

(22) PCT Filed: May 23, 2014

(86) PCT No.: PCT/EP2014/060617
§ 371 (c)(1),
(2) Date: Nov. 23, 2015

(87) PCT Pub. No.: WO2014/187937
PCT Pub. Date: Nov. 27, 2014

(65) Prior Publication Data
US 2016/0172578 A1    Jun. 16, 2016

(30) Foreign Application Priority Data

May 24, 2013  (FR) .................................... 13 54708

(51) Int. Cl.
*H01L 41/27* (2013.01)
*A61B 5/00* (2006.01)
(Continued)

(52) U.S. Cl.
CPC ............ *H01L 41/27* (2013.01); *A61B 5/0004* (2013.01); *A61B 5/0245* (2013.01);
(Continued)

(58) Field of Classification Search
None
See application file for complete search history.

(56) References Cited

U.S. PATENT DOCUMENTS 5,553,503 A  *  9/1996  Surdut .................. G01L 9/0001
                                                       73/760
7,554,251 B2 *  6/2009  Kondo ................ H01L 41/0471
                                                       310/363
(Continued)

FOREIGN PATENT DOCUMENTS

| EP | 1 126 530 A2 | 8/2001 |
| JP | 2006 204534 A | 8/2006 |
| WO | 2012/145278 A2 | 10/2012 |

OTHER PUBLICATIONS

Fujita T et al: "Flexible Sensor for Human Monitoring System by Using P(VDF/TrFE) Thin Film", Fifth International Conference on Emerging Trends in Engineering and Technology, Nov. 5-7, 2012, Himeji, Japan, 2012, pp. 75-79, XP032355108, DOI: 10 .1109/ ICETET. 2012. 22, Section I, IV, V, VI, figures 1, 11-15.
(Continued)

*Primary Examiner* — Brian T Gedeon
(74) *Attorney, Agent, or Firm* — Young & Thompson

(57) ABSTRACT

A method for producing a piezoelectric sensor, includes the following steps: producing, on a rigid support (10), a stack of sensor layers (2, 4, 5, 12), the sensor layers including a layer of piezoelectric material (5) included between a first electrode (6, 7) and a second electrode (8, 9), the first electrode not being in contact with the second electrode, then, while the sensor layers (2, 4, 5, 12) are still held by the rigid support (10), covering the sensor layers with a polymer
(Continued)

Figure 1:
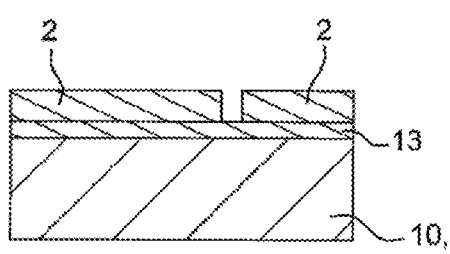

layer (11), then removing the stack of sensor layers from the rigid support (10), such that the sensor layers covered by the polymer layer (11) are no longer carried by the rigid support (10).

16 Claims, 6 Drawing Sheets

(51) Int. Cl.
*A61B 5/024* (2006.01)
*H01L 41/04* (2006.01)
*H01L 41/047* (2006.01)
*H01L 41/053* (2006.01)
*H01L 41/113* (2006.01)
*H01L 41/22* (2013.01)
*A61B 5/0245* (2006.01)
*H01L 41/083* (2006.01)

(52) U.S. Cl.
CPC .......... *A61B 5/02444* (2013.01); *H01L 41/04* (2013.01); *H01L 41/047* (2013.01); *H01L 41/0477* (2013.01); *H01L 41/0533* (2013.01); *H01L 41/083* (2013.01); *H01L 41/1132* (2013.01); *H01L 41/22* (2013.01); *A61B 2562/125* (2013.01)

(56) References Cited

U.S. PATENT DOCUMENTS

| | | | |
|---|---|---|---|
| 8,593,036 B2* | 11/2013 | Boysel | H01L 41/1136 310/339 |
| 8,680,751 B2* | 3/2014 | Wang | B82Y 30/00 257/43 |
| 8,721,055 B2* | 5/2014 | Shimizu | B41J 2/161 347/71 |
| 2007/0152537 A1 | 7/2007 | Yamaguchi et al. | |
| 2013/0134838 A1* | 5/2013 | Yun | H01L 41/047 310/366 |
| 2015/0380634 A1* | 12/2015 | Henn | H03H 9/0547 310/344 |

OTHER PUBLICATIONS

Morito Akiyama et al: "Flexible piezoelectric pressure sensors using oriented aluminium nitride thin films prepared on polyethylene terephthalate films" by Akiyama et al., Journal of Applied Physics vol. 100, 114318 (2006).

International Search Report, dated Sep. 26, 2014, from corresponding PCT application.

FR Search Report, dated Jan. 15, 2014, from corresponding PCT application.

\* cited by examiner

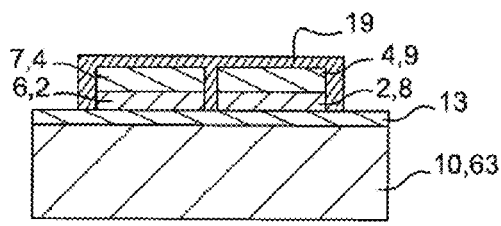
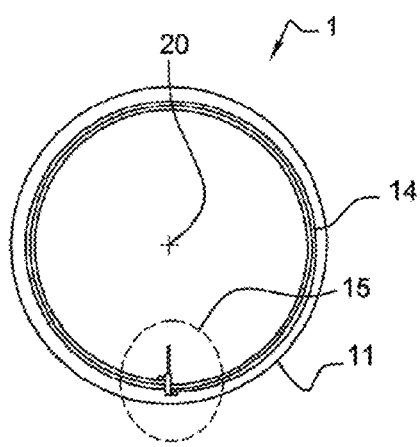
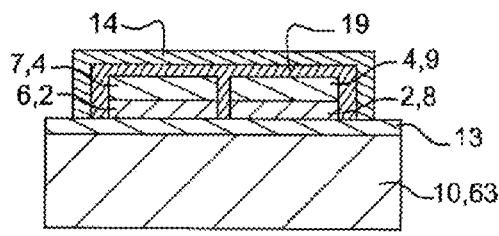
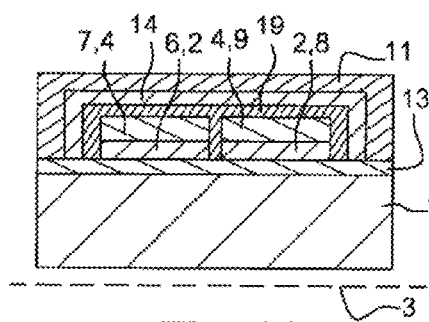
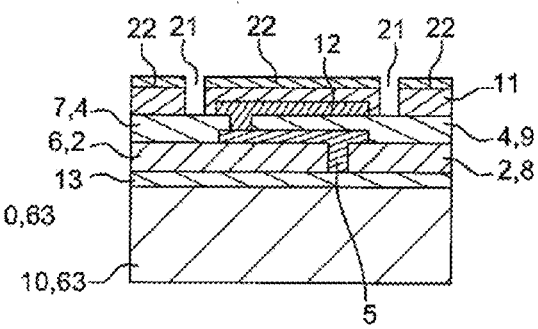
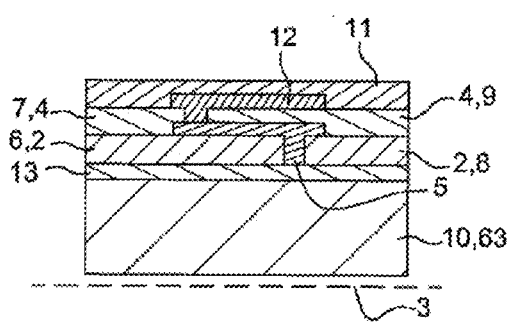
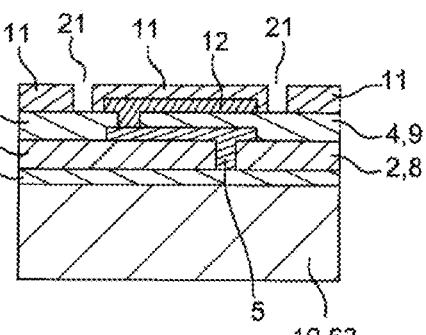

METHOD FOR PRODUCING A FLEXIBLE PIEZOELECTRIC SENSOR

TECHNICAL FIELD

The present invention relates to a process for producing a piezoelectric sensor. It also relates to a sensor produced by this production process, and a process for using such a sensor.

Such a production process allows a user to produce a "flexible" piezoelectric sensor.

The field of the invention is more particularly that of piezoelectric MEMS (micro-electro-mechanical systems) sensors, in particular for the detection of vibrations, beats, or deformations.

PRIOR ART

Process for producing piezoelectric sensors on flexible substrate are known, as for example described in the article entitled "*Flexible piezoelectric pressure sensors using oriented aluminium nitride thin films prepared on polyethylene terephthalate films*" by Akiyama et al., JOURNAL OF APPLIED PHYSICS vol. 100, 114318 (2006).

In this production process according to the state of the art, a very basic structure is produced: two electrodes on the two sides of a flexible PET film.

Drawbacks of this process according to the state of the art are that:
- this process according to the state of the art is not compatible with CMOS clean room technology, and
- this process according to the state of the art does not make it possible to produce complex structures (sensor in the form of a bar, round, square, etc.)

The purpose of the present invention is to resolve at least one of these drawbacks.

DISCLOSURE OF THE INVENTION

This objective is achieved with a process for producing a piezoelectric sensor, comprising the following steps:
- producing, on a support (preferably comprising a layer of silicon and/or a layer of silicon oxide; this support or these layers preferably having a total thickness of at least 400 micrometers), a stack of sensor layers, the sensor layers comprising a layer of piezoelectric material comprised between a first electrode and a second electrode, the first electrode not being in contact with the second electrode, then
- while the sensor layers are still carried by the support, coating the sensor layers with a first layer of polymer, then
- removing at least a part (preferably all) of the support from the stack of sensor layers, preferably so that the sensor layers coated with the first polymer layer are no longer carried by the support.

The removal of at least a part (preferably of all) of the support comprises destruction of at least a part (preferably of all) of the support. The removal of all of the support makes it possible to obtain a flexible and particularly thin piezoelectric sensor. This sensor is, moreover, self-supported.

After the removal of the at least a part of the support, it is possible to produce a second layer of polymer so that the sensor layers are encapsulated between the first polymer layer and the second polymer layer.

The encapsulation of the sensor layers by the first polymer layer and the second polymer layer makes it possible, on the one hand, to protect the sensor from external stresses while retaining its flexibility and, on the other hand, to make the sensor biocompatible and self-supported.

The polymer used for the first polymer layer and/or the second polymer layer according to the invention can be selected from the list constituted by Parylene or Polyimide.

Preferably, the first polymer layer and/or the second polymer layer is constituted by Parylene as it avoids the presence of a zone of fragility and its deposition does not alter the sensor according to the invention. Preferably, the first polymer layer and the second polymer layer are constituted by the same polymer. The thickness of the first polymer layer is at least 3 μm above the sensor. The thickness of the second polymer layer is at least 3 μm below the sensor. The thickness of each of the polymer layers is generally less than 50 μm and preferably less than 20 μm, more preferentially less than 10 μm.

The support is preferably a rigid support. Under standard ambient conditions of a temperature of 25° C. and absolute pressure of 0.986 atm. (standard atmospheric pressure unit), the rigid support preferably has a Young's modulus of at least 50 GPa (gigapascal), preferably at least 100 GPa, preferably comprised between 160 GPa and 180 GPa. As explained in the examples, the support preferably comprises silicon, such as for example glass, and more preferably it is constituted by silicon. In this case, the monocrystalline silicon can have an oxidized surface. With respect to a metal support, this type of support allows implementation of the invention in a clean room (using CMOS technology) and also makes it possible to obtain a sensor with more varied structures and, with respect to a polymer support, to obtain a thinner sensor and easier implementation.

The stack of sensor layers can comprise a first conductive layer and a second conductive layer, each of the first and second conductive layers comprising two parts, a first part of the first conductive layer being in contact with a first part of the second conductive layer, a second part of the first conductive layer being in contact with a second part of the second conductive layer, the first electrode being formed by the first part of the first conductive layer and by the first part of the second conductive layer, the second electrode being formed by the second part of the first conductive layer and by the second part of the second conductive layer, the layer of piezoelectric material being comprised at least in part between the first conductive layer and the second conductive layer. This advantageous embodiment in particular allows greater freedom in the allowed geometry of the sensor and possible use of aluminium for each conductive layer.

The conductive layers are preferably metallic. The conductive layers can be for example made of platinum, gold or aluminium. The use of aluminium makes it possible to reduce the production costs of the sensors whereas platinum is more suited to in vivo applications.

The process according to the invention can also comprise the production of an antenna linking the first electrode to the second electrode, said antenna making one or more turns so as to create a closed loop. Preferably, the thickness of the antenna is comprised between 10 and 50 μm. The antenna advantageously makes it possible to avoid the presence of a hole through the first polymer layer (i.e. for accessing the electrodes) and thus to completely encapsulate the sensor.

The process according to the invention can be carried out at a temperature less than 250° C. and thus allow the production of the sensor on a support incorporating integrated circuits. In certain cases, the support can have previously undergone preparation steps including passes at temperatures greater than 250° C.

The piezoelectric layer can be in the form of a bar extending longitudinally, and the bar can extend longitudinally from the perimeter of the loop towards the inside of the loop. This embodiment in particular makes it possible to measure deformations over greater surface areas and for example to carry out measurements of longitudinal and transverse deformation as well as of radii of curvature.

As stated, the invention relates in particular to a process compatible with CMOS clean room technology. Thus the piezoelectric layer is preferably constituted by $PbZrTiO_3$ (LZT, lead zirconate titanate), aluminium nitride (AlN) or PVDF (polyvinylidene fluoride). More preferably, as presented in the examples, the piezoelectric layer is constituted by AlN. An AlN layer, unlike a $PbZrTiO_3$ layer, is compatible with CMOS technology and it is not toxic.

The sensor layers can comprise:
- an insulating layer, produced between the antenna and the first electrode and produced between the antenna and the second electrode, at zones where the antenna is superimposed on the first electrode or the second electrode. The insulating layer can be produced from an electrically insulating material, having an electrical resistivity greater than or equal to $10^3$ ohm·cm (preferably $10^6$ ohm·cm) under standard ambient conditions of a temperature of 25° C. and absolute pressure of 0.986 atm; and/or
- a stiffening layer superimposed on the piezoelectric layer.

The stiffening layer, under standard ambient conditions of a temperature of 25° C. and absolute pressure of 0.986 atm., has a Young's modulus of at least 50 GPa, preferably of at least 100 GPa, preferably comprised between 100 GPa and 1 TPa.

The stiffening layer and the insulating layer are preferably produced from one and the same material during one and the same layer deposition step.

The total thickness of the sensor layers is preferably less than 3 micrometers.

As described in the examples, when it is encapsulated in a polymer, the final thickness of the sensor comprising an antenna is comprised between 10 and 50 μm. In the absence of an antenna, the thickness of the encapsulated sensor can be less than 50 μm, preferably less than 10 μm. In the absence of an antenna, the thickness of the encapsulated sensor is for example 10 μm.

According to yet another aspect of the invention, a sensor obtained by a production process according to the invention is proposed.

In particular, according to yet another aspect of the invention, a piezoelectric sensor comprising a layer of piezoelectric material comprised between a first electrode and a second electrode is proposed, the first electrode not being in contact with the second electrode, characterized in that said sensor is between two polymer layers and that it has a thickness, including the polymer layers, less than 50 μm, preferably less than 10 μm.

Preferably, said sensor comprises a layer of piezoelectric material constituted by AlN material.

According to yet another aspect of the invention, a process for using a sensor obtained according to the production process according to the invention is proposed, characterized in that the sensor is applied on or in a structure in order to measure at least one stress thereon, or at least one pressure applied to this structure.

According to yet another aspect of the invention, a process for using a sensor obtained according to the production process according to the invention is proposed, characterized in that it comprises the following steps:
- the sensor is applied on a human or animal body, then
- for each heartbeat of said body among several beats, the heartbeat deforms the piezoelectric layer, resulting in a variation in the electric charge on the electrodes.
- for each variation in electric charge, this variation in electric charge is detected, and
- a heart rate of the body is deduced from these detections.

According to yet another aspect of the invention, a process is proposed for using a sensor obtained according to the production process according to the invention, characterized in that it comprises the following steps:
- the sensor is applied on a human or animal body, then
- an electromagnetic field is emitted by excitation electronics, then
- the electromagnetic field is picked up by an antenna electrically connected to the first electrode and to the second electrode of the sensor, generating an electric current in the antenna with a frequency f1 equal to a resonance frequency f0 of the inactive sensor or to a harmonic of this resonance frequency f0,
- for each heartbeat of said body among several beats, the heartbeat deforms the piezoelectric layer, causing a variation Df in the resonance frequency,
- for each variation Df in the resonance frequency, a signal oscillating at a frequency f1+Df is received by the measurement electronics,
- a heart rate of the body is deduced from these detections.

DESCRIPTION OF THE FIGURES AND EMBODIMENTS

Figure 9:
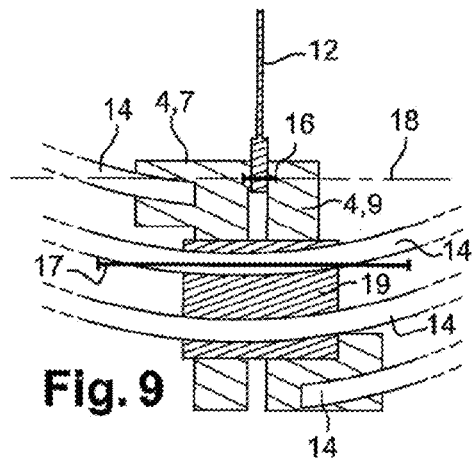
Figure 16:
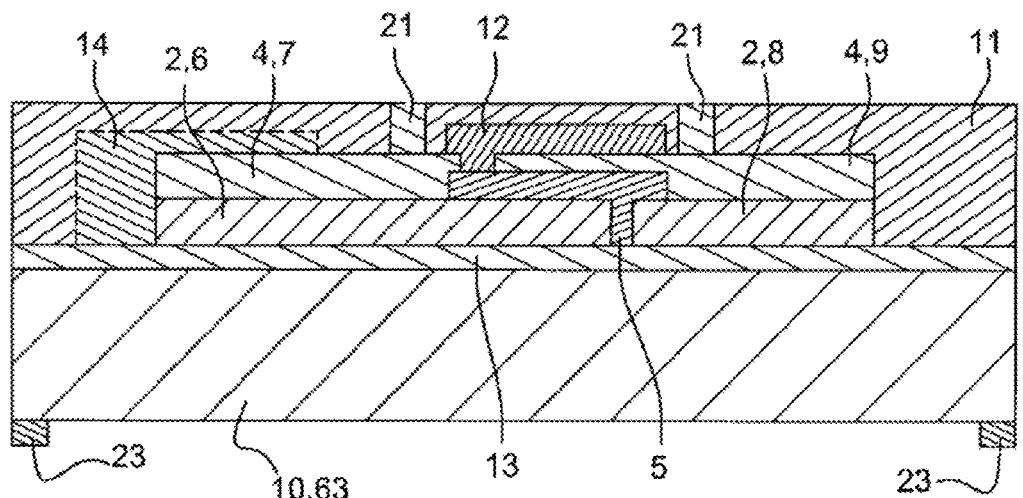
Figure 17:
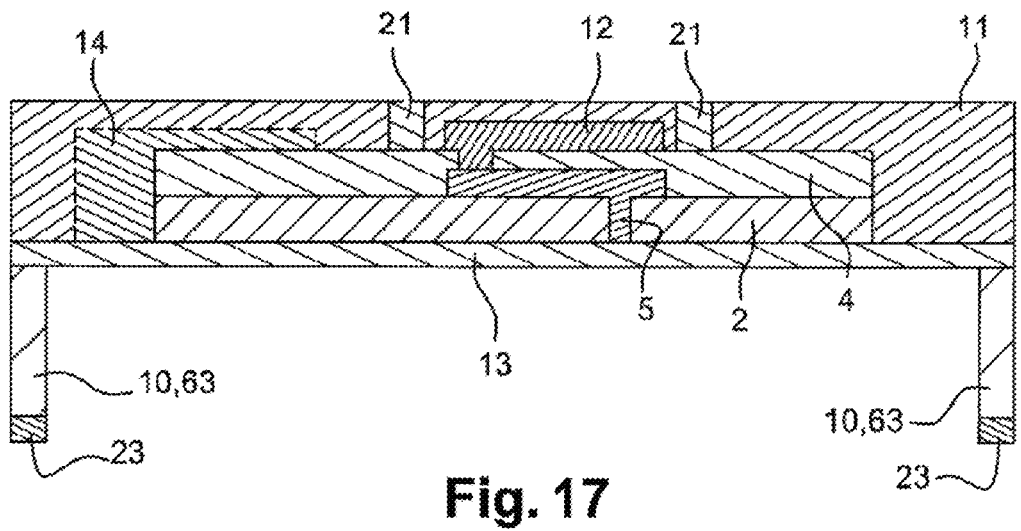
Figure 18:
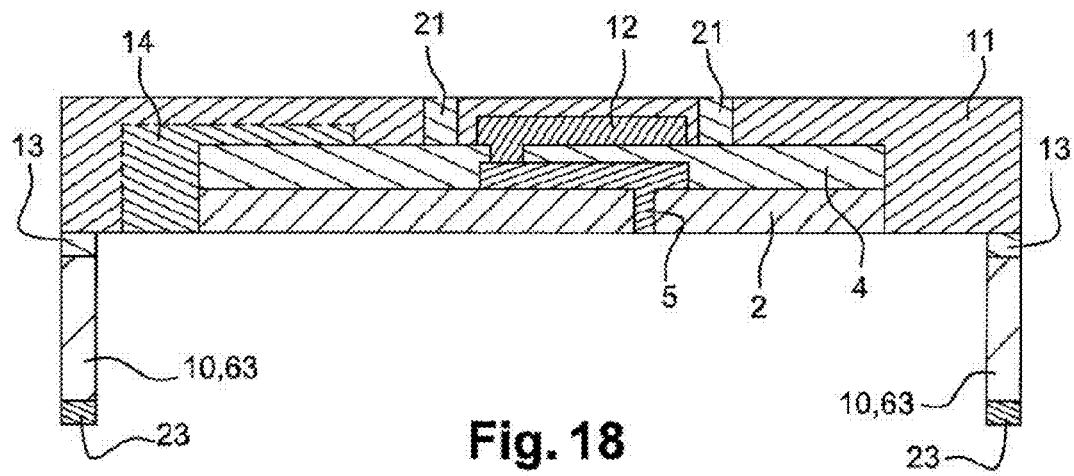
Figure 19:
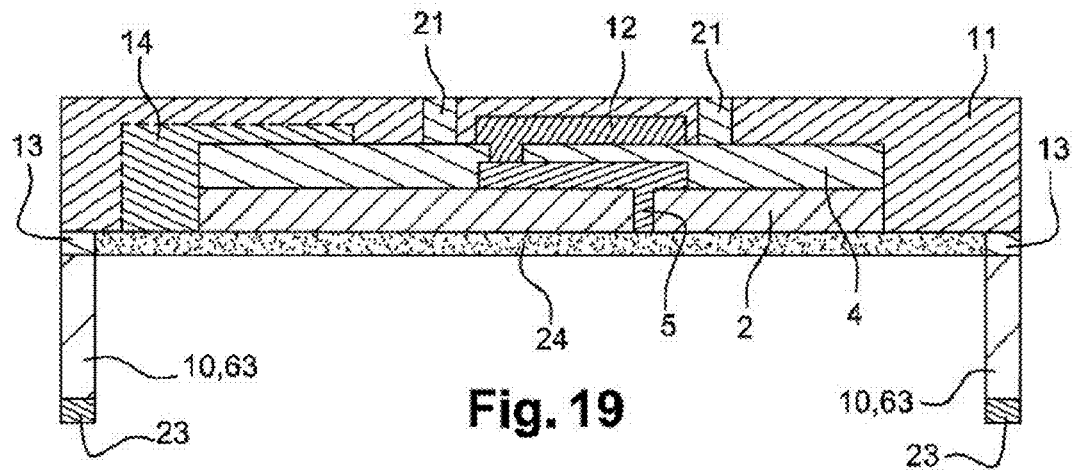
Figure 20:
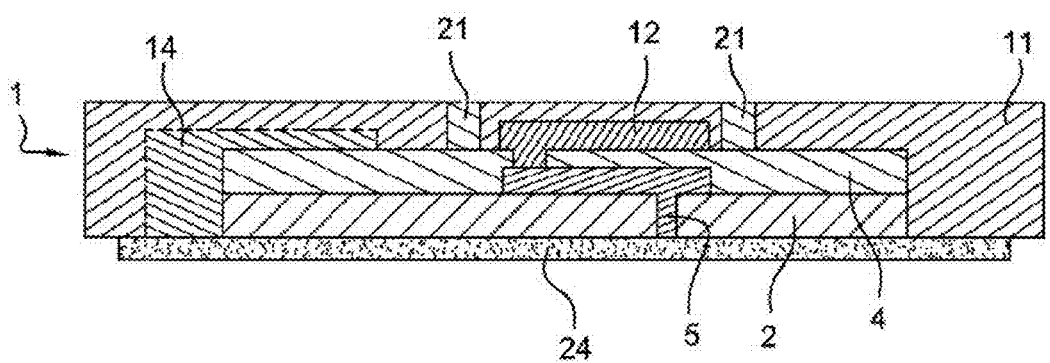
Figure 22:
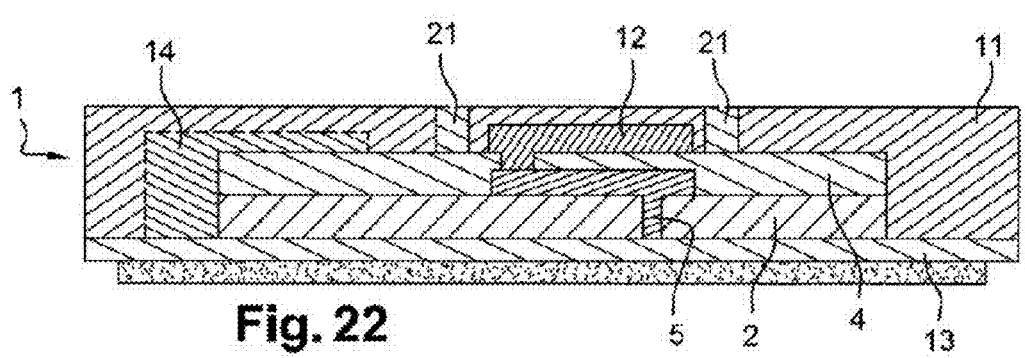
Figure 23:
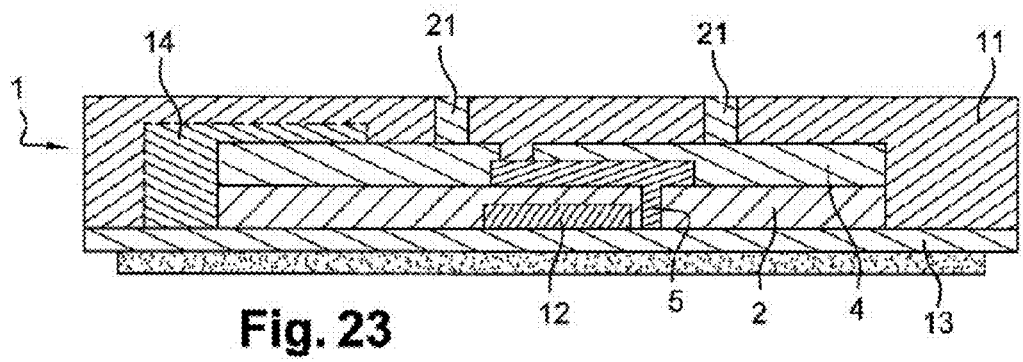
Figure 24:
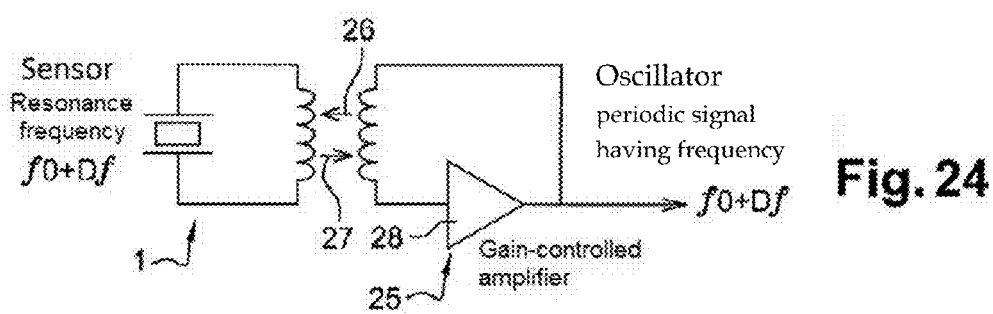
Figure 25:
Figure 26:
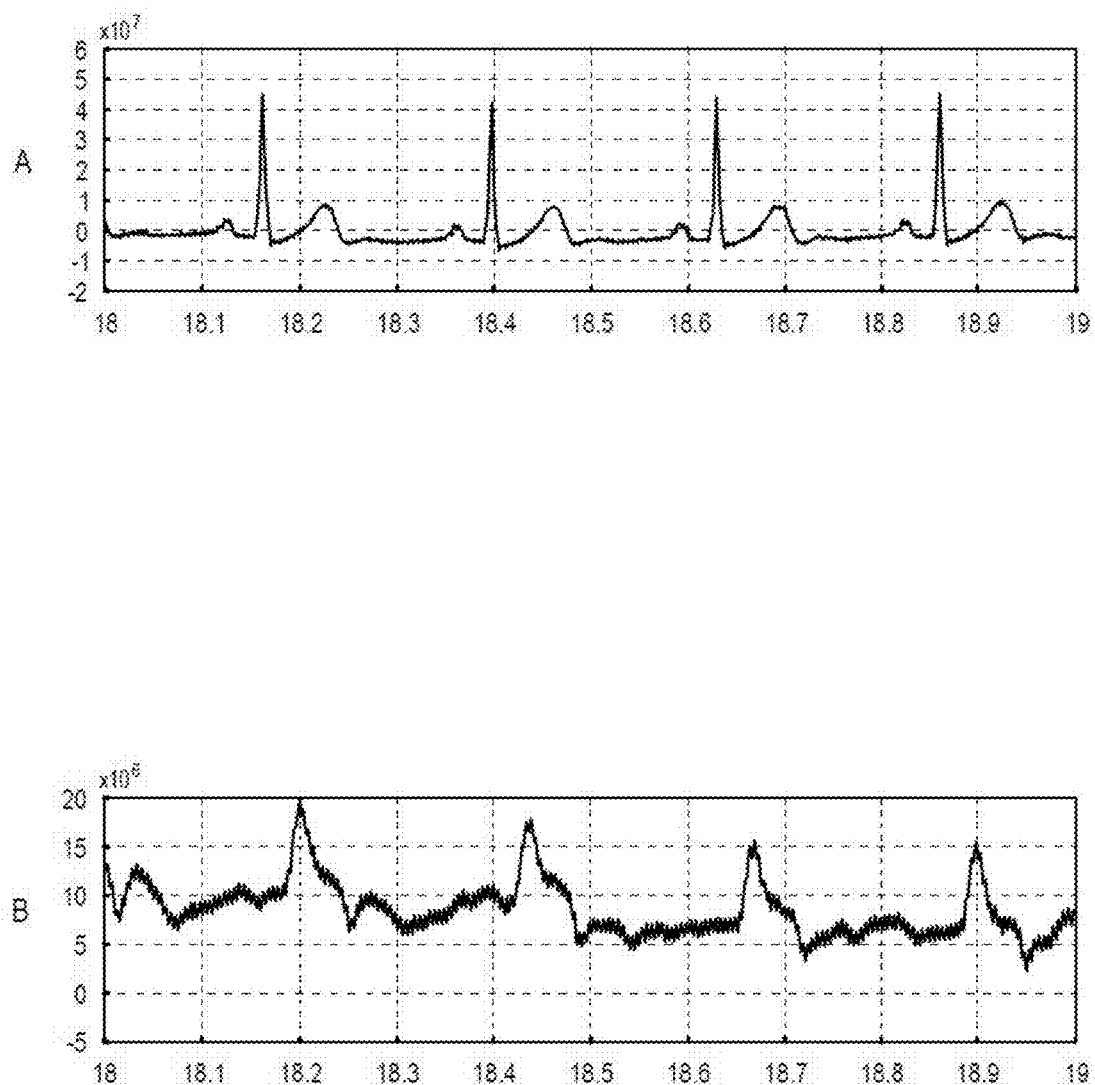

Other advantages and features of the invention will become apparent on reading the detailed description of implementations and embodiments that are in no way limitative, and the following attached drawings:

FIGS. 2, 4, 6, 9, 13 are top views, parallel to the plane of the layer referenced 3 in FIG. 11, of different layers at different steps of a first embodiment of the process according to the invention for producing a sensor 1, FIGS. 1, 3, 5, 7 and 12 are profile cross-sections (perpendicular to the plane of layer 3) of different layers at different steps of the first embodiment of the production process according to the invention; these cross-sections show the different layers along the first cut segment 16 shown in FIGS. 2, 4, 6, 9, FIGS. 8, 10, 11 are profile cross-sections (perpendicular to the plane of layer 3) of different layers at different steps of the first embodiment of the production process according to the invention; these cross-sections show the different layers along the second cut segment 17 shown in FIG. 9, FIGS. 14 and 15 are profile cross-sections (perpendicular to the plane of layer 3) of different layers at different steps of a variant (with respect to the variant with antenna 14) of the first embodiment of the production process according to the invention; these cross-sections show the different layers along the first cut segment 16 shown in FIGS. 2, 4, 6, 9, FIGS. 16 to 19 are profile cross-sections (perpendicular to the plane of layer 3) of different layers at different steps of the first embodiment of the production process according to the invention; these cross-sections show the different layers along the cross-section axis 18 shown in FIG. 9, FIG. 20 is a profile cross-section (perpendicular to the plane of layer 3) of the sensor 1 obtained by the first embodiment of the production process according to the invention; this cross-section shows the different layers of this sensor along the cut axis 18 shown in FIG. 9, FIGS. 21 to 23 are profile cross-sections (perpendicular to the plane of layer 3) of different variants of the sensor 1 obtained by different variants of the first embodiment of the production process according to the invention; these cross-sections show the different layers of the sensor 1 along the cut axis 18 shown in FIG. 9, FIG. 24 is a diagram of the electronics for the use of the sensor 1, FIG. 25 is a flowchart of the principle of the electronics for the use of the sensor 1, FIG. 26 is an example of the use of the sensor 1 according to the invention.

In the description below, each thickness is defined perpendicular to the plane of layer 3.

The respective proportions of the thicknesses and widths of the different layers are not respected in the profile views.

As these embodiments are in no way limitative, it will be possible in particular to consider variants of the invention comprising only a selection of characteristics described hereafter in isolation from the other characteristics described (even if this selection is isolated within a sentence including these other characteristics), if this selection of characteristics is sufficient to confer a technical advantage or to differentiate the invention with respect to the prior art. This selection comprises at least one, preferably functional, characteristic without structural details, or with only a part of the structural details if this part alone is sufficient to provide a technical advantage or to distinguish the invention from the prior art.

Firstly, a first embodiment of the production process according to the invention will be described with reference to FIGS. 1 to 20.

This first embodiment of the process according to the invention for producing a piezoelectric sensor 1 comprises the following steps:

producing, on a rigid support 10, a stack (in a stack direction perpendicular to the plane of layer 3) of sensor layers 2, 4, 5, 12, 19, each sensor layer being produced by photolithography, the sensor layers comprising a layer of piezoelectric material 5 (extending at least in part parallel to the plane of layer 3) comprised between a first electrode 6, 7 (extending at least in part parallel to the plane of layer 3) and a second electrode 8, 9 (extending at least in part parallel to the plane of layer 3), the first electrode not being in contact with the second electrode, then while the sensor layers 2, 4, 5, 12, 19 are still carried by the rigid support 10, coating the sensor layers with a polymer layer 11, then removing the stack of sensor layers from the rigid support 10, so that the sensor layers coated with the polymer layer 11 are no longer carried by the rigid support 10.

As will be seen hereafter, this process according to the invention is compatible with CMOS clean room technology, and makes it possible to produce complex structures.

Production of the Stack of Sensor Layers 2, 4, 5, 12, 19 on the Rigid Support 10

For production of the sensor layers 2, 4, 5, 12, 19, a material (preferably silicon) having under standard ambient conditions of a temperature of 25° C. and absolute pressure of 0.986 atm., a Young's modulus of at least 50 GPa (gigapascal), more particularly of at least 100 GPa, preferably comprised between 160 GPa and 180 GPa, is used as rigid support 10.

In this description, all the Young's modulus values are defined along an axis perpendicular to the plane of layer 3 shown in FIG. 11.

The rigid support 10 typically comprises (or even preferably consists of) a non-oxidized silicon layer 63.

An oxidized silicon layer 13 is in contact with the non-oxidized silicon layer 63. According to the variant considered, this oxidized layer 13 forms part of the rigid support 10 or forms part of the sensor layers, according to whether or not this layer 13 is retained for the sensor 1.

The rigid support 10 has, a thickness of at least 400 μm in the stack direction perpendicular to the plane of layer 3.

The stack of sensor layers comprises a first electrically conductive layer 2 (preferably metallic, typically made of aluminium) extending parallel to the plane of layer 3, and a second electrically conductive layer 4 (preferably metallic, typically made of aluminium) extending parallel to the plane of layer 3.

Each of the first 2 and second 4 conductive layers has an electrical resistivity less than or equal to 3 ohm·cm (preferably less than or equal to $10^{-4}$ ohm·cm or even $10^{-6}$ ohm·cm).

Each of the first 2 and second 4 conductive layers comprises two parts: a first part 6 of the first conductive layer is in contact with a first part 7 of the second conductive layer; a second part 8 of the first conductive layer is in contact with a second part 9 of the second conductive layer.

The first electrode 6, 7 is formed by the first part 6 of the first conductive layer and by the first part 7 of the second conductive layer.

The second electrode 8, 9 is formed by the second part 8 of the first conductive layer and by the second part 9 of the second conductive layer.

The layer of piezoelectric material 5 is comprised at least in part between the first conductive layer 2 and the second conductive layer 4.

The layer of piezoelectric material 5 is in contact with the first electrode (preferably with each of the parts 6, 7).

The layer of piezoelectric material 5 is in contact with the second electrode (preferably with each of the parts 8, 9).

The first electrode 6, 7 is not in contact with the second electrode 8, 9. Electric current passing between the two electrodes must necessarily pass, among the sensor layers, via the piezoelectric material layer 5 or, outside the sensor layers, via the antenna 14 described hereafter.

Figure 2:
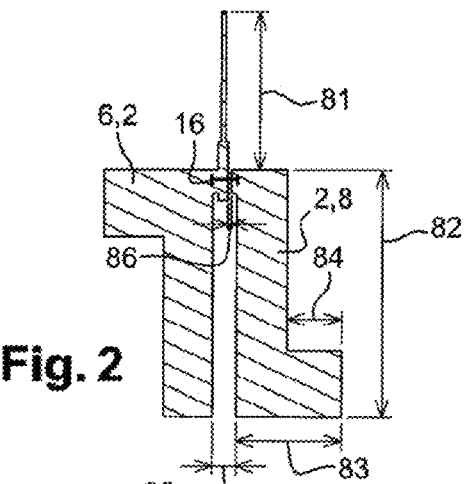

With reference to FIGS. 1 and 2, the first conductive layer 2 made of aluminium is produced by photolithography according to the following steps:

Cleaning a silicon wafer

Oxidation of the silicon wafer at 1050° C. with a mixture of H and $O_2$ gases ("wet oxidation")/Obtained thickness of the oxidized layer 13 equal to 1.6 μm, on the non-oxidized silicon layer 63.

Deposition of metal (aluminium), thickness of 200 nm above the layer 13, under argon: $0.5 \times 10^{-2}$ mbar (pressure in the chamber/for 5 min/at 200 watt of power from the DC generator, supplying the aluminium target Positive light-sensitive resin photolithography (PFR7790 from JSR);

thickness 1.1 μm

Spread speed: 4500 rpm for 30 seconds

"Soft Bake" on hotplate: 3 min at 110° C.

Exposure through a mask for 4 seconds at 6.5 mW/cm² of UV light intensity

Development of the resin (PRD238 developer from OMG) for 1 min

Rinsing with deionized water

"Hard Bake" on hotplate: 3 min at 110° C.

Liquid etching (Al etch ANT 760-30-150 from OMG) for aluminium attack

For 3 min/Rinsing with deionized water

Removal of the resin: use of acetone, then isopropyl alcohol, then deionized water as solvent.

Figure 3:
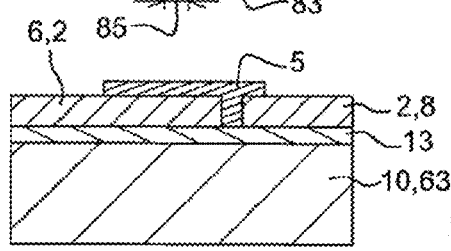
Figure 4:
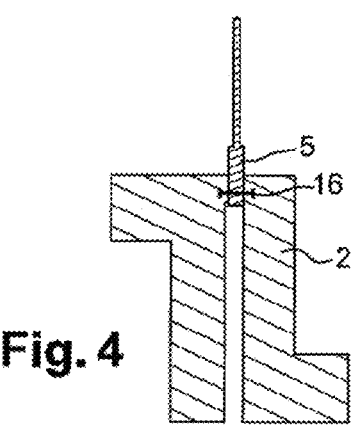

The dimensions referenced 81 to 86 in FIG. 2 have the following values:

Reference 81 (shortened in the top views of FIGS. 2, 4, 6, 9 with respect to the other dimensions): 1 centimeter Reference 82: 2 millimeters Reference 83: 1 millimeter Reference 84: 0.5 millimeter Reference 85: 0.2 millimeter Reference 86: 20 micrometers With reference to FIGS. 3 and 4, the piezoelectric material layer 5 made of aluminium nitride is produced by photolithography on the first conductive layer 2 according to the following steps:

Deposition of AlN (aluminium nitride) by reactive sputtering

Thickness of 1 µm above the layer 2, under:

Argon: $1.9 \times 10^{-2}$ mbar (partial pressure) and

Nitrogen: $3.4 \times 10^{-2}$ mbar (partial pressure)

for 1 h/at 500 W (DC power of the generator)/at 220° C. (temperature of the substrate) with a residual vacuum before deposition less than $2.5 \times 10^{-7}$ Torr Light-sensitive resin photolithography PFR7790 thickness 1.1 µm

Spread speed: 4500 rpm for 30 seconds

"Soft Bake" on hotplate: 3 min at 110° C.

Exposure through a mask for 4 seconds at 6.5 mW/cm² of UV light intensity

Development of the resin (PRD238 developer from OMG) for 1 min

Rinsing with deionized water

"Hard Bake" on hotplate: 3 min at 110° C.

Liquid etching (PRD 238 from OMG)

For 3 min/Rinsing with deionized water

Removal of the resin: use of acetone, then isopropyl alcohol then deionized water, as solvent.

Generally, it is possible to use other piezoelectric materials, such as LZT (lead zirconate titanate), or PVDF (polyvinylidene fluoride).

Figure 5:
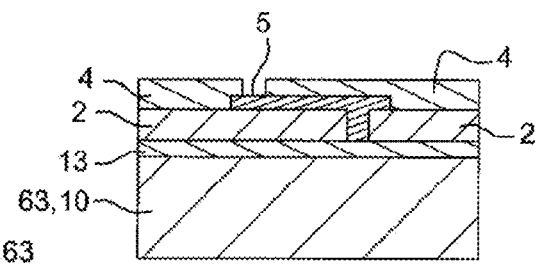
Figure 6:
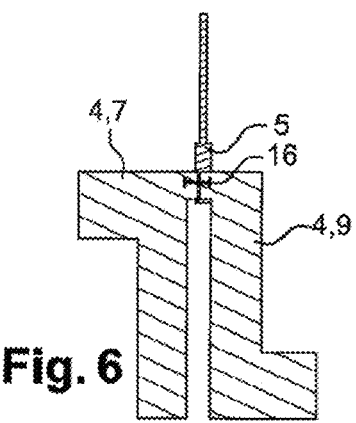

With reference to FIGS. 5 and 6, the second conductive layer 4 made of aluminium is produced by photolithography on the first conductive layer 2 and on the piezoelectric material layer 5 according to the following steps:

Deposition of metal (aluminium), thickness of 200 nm above the layer 2 and of 200 nm above the layer 5 (unlike the diagrammatic representation of the profile views of FIGS. 5, 7, 12, 14, 15 and 16 to 23, the upper face of the conductive layer 4 in these figures is not flat but is stepped so as to have substantially one and the same thickness above each of the layers 2 and 5) under argon: $0.5 \times 10^{-2}$ mbar (pressure in the chamber)/for 5 min/at 200 watt of power from the DC generator, supplying the aluminium target Positive light-sensitive resin photolithography (PFR7790 from JSR);

thickness 1.1 µm

Spread speed: 4500 rpm for 30 sec

"Soft Bake" on hotplate: 3 minutes at 110° C.

Exposure through a mask for 4 seconds at 6.5 mW/cm² of UV light intensity

Development of the resin (PRD238 developer from OMG) for 1 min

Rinsing with deionized water

"Hard Bake" on hotplate: 3 min at 110°

Liquid etching (Al etch ANT 760-30-150 from OMG) for aluminium attack

For 3 min/Rinsing with deionized water

Removal of the resin: use of acetone, then isopropyl alcohol, then deionized water as solvent.

Figure 7:
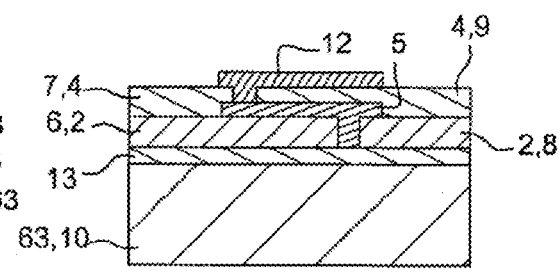

With reference to FIGS. 7, 8 and 9, a stiffening layer 12 made of nitride ($Si_3N_4$) superimposed on the piezoelectric layer 5 is produced by photolithography at the same time as an insulating layer 19 made of nitride ($Si_3N_4$). The insulating layer 19 is produced from an electrically insulating material (in this case nitride ($Si_3N_4$)), having an electrical resistivity greater than or equal to $10^3$ ohm·cm (preferably $10^6$ ohm·cm) under standard ambient conditions of a temperature of 25° C. and absolute pressure of 0.986 atm. The stiffening layer made of nitride 12 ($Si_3N_4$) is produced on the second conductive layer 4 and on the piezoelectric material layer 5 (preferably over the entire upper surface of the piezoelectric layer) and the insulating layer 19 is produced on the second conductive layer 4 according to the following steps:

Deposition of nitride ($Si_3N_4$) in PECVD (plasma enhanced chemical vapour deposition) phase, thickness of this layer: 1 µm above the layer 4 and the layer 19.

Positive light-sensitive resin photolithography (PFR7790 from JSR);

thickness 1.1 µm

Spread speed: 4500 rpm for 30 seconds

"Soft Bake" on hotplate: 3 minutes at 110° C.

Exposure through a mask for 4 seconds at 6.5 mW/cm² of UV light intensity

Development of the resin (PRD238 developer from OMG) for 1 min

Rinsing with deionized water

"Hard Bake" on hotplate: 3 min at 110° C.

RIE (Reactive Ion Etching) with $SF_6$ (sulphur hexafluoride)

Flow rate of 10 sccm/partial pressure of 20 mTorr in the chamber/30 Watt of power from the radio frequency generator Removal of the resin: use of acetone, then isopropyl alcohol, then deionized water as solvent.

Thus the stiffening layer 12 and the insulating layer 19 are produced from one and the same material during one and the same layer deposition step by photolithography.

The stiffening layer 12, under standard ambient temperature and pressure conditions of 25° C. and absolute pressure of 0.986 atm., has a Young's modulus greater than that of the rigid support 10.

The stiffening layer 12, under standard ambient temperature and pressure conditions of 25° C. and absolute pressure of 0.986 atm., has a Young's modulus of at least 50 GPa, more particularly of at least 100 GPa, preferably comprised between 100 GPa and 1 TPa (terapascal). The role of this stiffening layer 12 is to define the mechanical properties of vibrations of the piezoelectric layer, in particular its resonance frequency.

The stiffening layer has a thickness of at least 1 µm above the layer 4 and the layer 19.

With reference to FIGS. 9, 10 and 13 (FIG. 9 corresponding to the enlargement of the zone 15 delimited in FIG. 13), the first embodiment of the process according to the invention also comprises the production of an antenna 14 linking the first electrode 6, 7 to the second electrode 8, 9, said antenna 14 making at least one (preferably several) turns around a centre 20 (for example three turns as shown in FIG. 13) so as to create a closed loop.

The metal antenna 14 (typically made of copper or gold) is produced by electrodeposition on the first electrode 7 and on the second electrode 9 (more precisely on the second conductive layer 4) and on the insulating layer 19, according to the following steps:

Production of a thin seed layer (thickness comprised between 50 and 100 nm) typically made of copper or gold
definition of the mould made of thick resin
electrolytic deposition of copper or gold
Removal of the resin mould The thickness of the antenna 14 is comprised between 10 and 50 µm above the layer 13.

In the case shown in FIG. 13 where the layer of piezoelectric material 5 is in the form of a bar extending longitudinally, this bar extends longitudinally parallel to the plane of layer 3 from the perimeter of the loop and towards the inside of the loop, preferably towards the centre 20 of the loop.

The antenna comprises two ends and makes N turns around the centre 20 (with N a natural number): a first of its ends is electrically connected to the first electrode 6, 7, a second of its ends is connected to the second electrode 8, 9, and the antenna 14 passes N−1 times above the first electrode and the second electrode without being in contact with these electrodes for each of these passes. In fact, the insulating layer 19 is produced between the antenna 14 and the first electrode 6, 7 and produced between the antenna 14 and the second electrode 8, 9, at each of these N−1 passes where the antenna 14 is superimposed on the first electrode 6, 7 or the second electrode 8, 9 so as to avoid any short circuiting between the first electrode 6, 7 and the second electrode 8, 9.

The total thickness of the sensor layers 2, 4, 5, 12, 19 (and therefore without the antenna 14 and without the polymer layer 11) is less than 3 micrometers.

Coating of the Sensor Layers with the Polymer Layer 11

For the layer 11 (preferably as well as for the layer 24 introduced hereafter) a polymer is used which, under standard ambient temperature and pressure conditions of 25° C. and absolute pressure of 0.986 atm., has a Young's modulus less than 50 GPa, more particularly less than 1 MPa (megapascal), preferably comprised between 0.3 MPa and 1 MPa.

The thickness of the polymer layer 11 is a minimum of 3 µm above the sensor layers 2, 4, 5, 12, 19.

The polymer layer 11 is produced by a deposition of Parylene (SCS equipment) or Polyimide 2611 (final thickness between 20 and 60 µm above the layer 13, depending on the thickness of the antenna 14 comprised between 10 and 50 µm above the layer 13).

The first 6, 7 and second 8, 9 electrodes and the piezoelectric layer 5 (as well as the antenna 14, the stiffening layer 12 and the insulating layer 19) are situated between the polymer layer 11 and the rigid support 10.

Variant of the First Embodiment of the Process According to the Invention

With reference to FIGS. 14 and 15, in a variant of the first embodiment of the production process according to the invention the first steps of which have just been described, the antenna 14 and the insulating layer 19 are not produced.

Instead, after the production of the polymer layer 11, a part of the first electrode 6, 7 is "released" by removing a part of the polymer layer 11 in contact with the first electrode 6, 7 and a part of the second electrode 8, 9 is "released" by removing a part of the polymer layer 11 in contact with the second electrode 8, 9.

To this end, for each of the electrodes a hole 21 is made through the polymer layer 11 allowing access to each of these electrodes for an electric connection from the outside of the sensor 1.

Each of these holes 21 is made (preferably simultaneously) according to the following steps:

Deposition of a layer of metal 22 (titanium) with a thickness of 500 nm under argon at $1\times10^{-2}$ mbar/for 5 min
Positive light-sensitive resin photolithography (PFR7790 from JSR);
thickness 1.1 µm
Spread speed: 4500 rpm for 30 sec
"Soft Bake" on hotplate: 3 minutes at 110° C.
Exposure through a mask for 4 seconds at 6.5 mW/cm² of UV light intensity
Development of the resin (PRD238 developer from OMG) for 1 min
Rinsing with deionized water
"Hard Bake" on hotplate: 3 min at 110° C.
Liquid etching (30% hydrogen peroxide) of the layer 22 of titanium for 3 min/rinsing with deionized water
Oxygen plasma etching of the polymer layer 11 through the etching of the titanium layer 22 in order to form each hole 21
Removal of the titanium layer 22: use of 30% hydrogen peroxide as solvent Removal of the Rigid Support 10

Irrespective of the variant of the first embodiment of the process according to the invention (with the antenna 14 or with the holes 21), after deposition of the polymer layer 11, the stack of sensor layers is removed from the rigid support 10, so that the sensor layers coated with the polymer layer 11 are no longer carried by the rigid support 10.

In order to remove the sensor layers from the rigid support 10, the rigid support 10 is at least partially destroyed.

With reference to FIGS. 16 to 20, the procedure is as follows:

Deposition of a metal layer 23 (aluminium) with a thickness of 500 nm Under argon at $1\times10^{-2}$ mbar/for 5 min
Positive light-sensitive resin photolithography (PFR7790 from JSR);
thickness 1.1 µm
Spread speed: 4500 rpm for 30 seconds
"Soft Bake" on hotplate: 3 minutes at 110° C.
Exposure through a mask for 4 seconds at 6.5 mW/cm² of UV light intensity
Development of the resin (PRD238 developer from OMG) for 1 min
Rinsing with deionized water
"Hard Bake" on hotplate: 3 min at 110° C.
Liquid etching (Al etch ANT 760-30-150 from OMG), attack on the layer of aluminium 23 (protection of the front face is carried out in order not to etch the aluminium on the front face, e.g. deposition of resin)
For 3 min/Rinsing with deionized water
Removal of the resin: use of acetone, then isopropyl alcohol, then deionized water as solvent.
Deep reactive ion etching (DRIE) $SF_6$ (sulphur hexafluoride)/$C_4F_8$ (octafluorocyclobutane) of the layer of silicon 63, stopped by the oxide layer 13 (result obtained shown in FIG. 17)
Reactive ion etching (RIE) $SF_6$ (sulphur hexafluoride) and $CHF_3$ (trifluoromethane) of the oxide layer 13 (result obtained shown in FIG. 18)
Deposition on the rear face (i.e. where the rigid support 10 was situated before being partially destroyed) of a new polymer layer 24 (preferably the same polymer as for layer 11) or of adhesive in order to create a self-adhesive surface (result obtained shown in FIG. 19)

Cutting out the structures: whatever remains of layers 23, 63 and 13 is removed (result obtained shown in FIG. 20).

All of FIGS. 16 to 20 (as well as the following 21 to 23) are represented with hatched holes 21 and a dotted outline of antenna 14, according to whether it is considered whether these holes are hollow (variant without antenna 14) or these holes are filled with polymer and are not hollow (variant with antenna 14).

In FIG. 20, it is noted that the second polymer layer 24 is produced (after the removal of the at least a part of the support 10) so that the sensor layers are encapsulated (i.e. contained and preferably enclosed) between the first polymer layer 11 and the second polymer layer 24.

Figure 21:
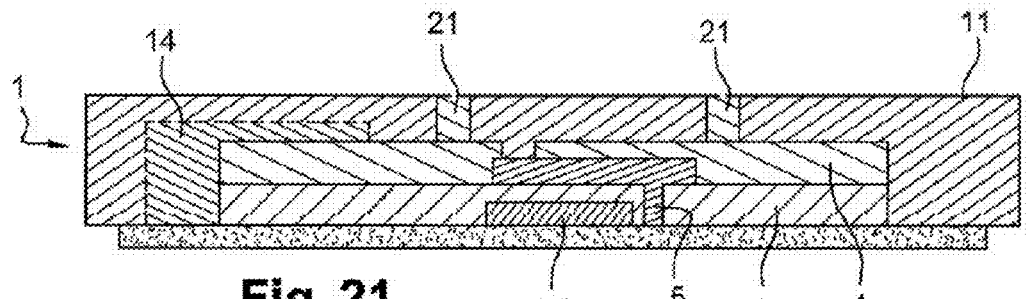

Other Variants of the First Embodiment of the Process According to the Invention With reference to FIGS. 21 and 23, the stiffening layer 12 can be produced before the first electrode 6, 7 and the second electrode 8, 9 (and therefore before the insulating layer 19).

During the production of the sensor 1, the stiffening layer 12 is therefore not situated between the electrodes, 6, 7, 8, 9 and the polymer layer 11 (preceding case in FIG. 20) but is situated between the electrodes 6, 7, 8, 9 and the rigid support 10.

With reference to FIGS. 22 and 23, the silicon oxide layer 13 can form part of the sensor layers; in this case, it is not destroyed or removed.

First Process for Using the Sensor 1.

A first embodiment of the process for using the sensor 1 according to the invention is a "passive" embodiment not requiring any excitation external to the sensor 1 apart from the signal to be detected.

In this first embodiment:
the sensor 1 is applied (for example by means of a self-adhesive surface 24) to an object (human or animal body, or inert object which is neither human nor animal) then
for each beat or vibration or deformation of said objet, the beat or vibration or deformation deforms the piezoelectric layer 5, generating a variation in electric charge in the electrodes 6, 7; 8, 9.
for each variation in electric charge, this variation in electric charge is detected.

In the particular case of periodic beats or vibrations or deformations, a frequency or a time period of these periodic beats or vibrations or deformations is then deduced from this detection.

For example:
the sensor is applied (for example via a self-adhesive surface) on a human or animal body (close to a vein or artery), then
for each heartbeat of said body among several beats, the heartbeat deforms the vein and the surrounding skin which leads to a deformation of the piezoelectric layer 5, generating a variation in electric charge in the electrodes 6, 7; 8, 9 (proportional to the deformation of the vein (amplitude and time)).
for each variation in electric charge, this variation in electric charge is detected, and
a heart rate or cardiac period of the body is deduced from these detections.

Second Process for Using the Sensor 1 (with or without Antenna 14 Incorporated).

A second embodiment of the process for using the sensor 1 according to the invention is an "active" embodiment requiring excitation external to the sensor 1 in addition to the signal to be detected.

In this second embodiment:
the sensor 1 is applied (for example by means of a self-adhesive surface 24) to an object (human or animal body, or inert object which is neither human nor animal), then
an electromagnetic field 26 is emitted by excitation electronics 25, then
the electromagnetic field 26 is picked up by the antenna 14 or by an antenna connected to the electrodes 6, 7 and 8, 9 through the holes 21, generating an electric current in this antenna, at a frequency f1 equal to a resonance frequency f0 of the inactive sensor (i.e. in the absence of stress and deformation of the piezoelectric layer 5 which is relaxed) or to a harmonic of this resonance frequency f0,
for each beat or vibration or deformation of said objet among several beats or vibrations or deformations, the beat or vibration or deformation deforms the piezoelectric layer 5, causing a variation Df in the resonance frequency,
for each variation Df in the resonance frequency, a signal 27 oscillating at a frequency f1+Df is received by measurement electronics 25,
a frequency or time period of the beats or vibrations or deformations is deduced from these detections.

For example:
the sensor is applied (for example via a self-adhesive surface) on a human or animal body (close to a vein or artery), then
an electromagnetic field 26 is emitted by excitation electronics 25, then
the electromagnetic field 26 is picked up by the antenna 14 or by an antenna connected to the electrodes 6, 7 and 8, 9 through the holes 21, generating an electric current in this antenna, at a frequency f1 equal to a resonance frequency f0 of the inactive at rest (i.e. in the absence of stress and deformation of the piezoelectric layer 5 which is relaxed) or to a harmonic of this resonance frequency f0,
for each heartbeat of said body among several beats, the heartbeat deforms the vein and the surrounding skin which leads to a deformation of the piezoelectric layer 5, causing a variation Df in the resonance frequency,
for each variation Df in the resonance frequency, a signal 27 oscillating at a frequency f1+Df is received by measurement electronics 25,
a heart rate or cardiac period of the body is deduced from these detections.

The excitation electronics and the measurement electronics are shown in FIGS. 24 and 25.

With reference to FIG. 24, the sensor 1 is excited at its fundamental resonance frequency (mechanical) or at a harmonic (mechanical).

At these frequencies the sensor 1 behaves as an RLC series filter in parallel with a static capacitor $C_0$.

A gain controlled amplifier 28 loops back on itself through the primary of a transformer (mutual inductance between the two windings), the sensor being connected to the secondary.

The circuit behaves as an oscillator the frequency of which depends on the operating frequency of the sensor 1 (mechanical fundamental resonance or harmonic frequency).

The variation in frequency is due to the variation in mechanical stress applied to the sensor.

In-vivo use of this sensor can be envisaged by carefully selecting the materials used and by encapsulating the sensor in a specific packaging (for example "Titanium polymer" in a thin layer)

With reference to FIG. 25, the sinusoidal signal 27 is converted to a square wave signal using a comparator, then the frequency $f_0+Df$ is measured using a counter, the value of the frequency is determined in digital format, then the signal is processed.

FIG. 26 presents the results of a use of a sensor according to the invention. A sensor produced according to the process of the invention makes it possible to measure the arterial deformation induced by the influx of blood (pulse wave) and thus provides information in agreement with the electrocardiograph or ECG (identification of the electric activity of the heart). As this measurement is based on physical amplitudes, the sensor can provide hitherto inaccessible additional information, such as the stresses applied to the arteries (elasticity, congestion etc.). Moreover, given the thinness of the sensor, in particular of the polymer layers encapsulating it and its flexibility, it allows sensitive and continuous measurement (e.g. it can be used during a subject's activities).

Part A of FIG. 26 is an ECG curve obtained on a healthy 30-year-old subject, using commercial electrodes of the COMEPA type and a commercial medical instrumentation amplifier (X-axis: arbitrary time unit; Y-axis: arbitrary unit).

Part B of FIG. 26 is a curve obtained on this same subject simultaneously with part A with a sensor according to the invention corresponding to the embodiment shown in FIG. 20 (but without antenna 14), by implementing a measurement process which has just been described, this sensor being attached over the subject's jugular vein by means of a sticking plaster (X-axis: arbitrary time unit; Y-axis: arbitrary unit).

Of course, the invention is not limited to the examples which have just been described and numerous adjustments can be made to these examples without exceeding the scope of the invention.

For example, viewed from above, the piezoelectric layer 5 may not necessarily have the form of a bar, but can have the form of a cross, a circular form or the form of interdigitated fingers.

Furthermore, it is possible to replace the layers of silicon 63 and of silicon oxide 13 with a rigid support 10 made of glass.

It is moreover possible not to remove all of the rigid support 10 but rather to leave a part of the rigid support 10 (this remaining part then no longer having the role of bearing the sensor layers) for example below the piezoelectric layer in order to leave a mass for other operating modes of the sensors (e.g.: microphone).

In a variant of FIG. 19, the polymer layer 24 also covers the parts numbered 10, 63 and 23.

In a variant of each of FIGS. 20, 21, 22 and 23, (after cutting out) the "width" (defined horizontally in the plane of these figures) of the polymer layer 11 is reduced to the "width" of the polymer layer 24 which defines the size of the sensor.

Of course, the different characteristics, forms, variants and embodiments of the invention can be combined with one another according to various combinations inasmuch as they are not incompatible or mutually exclusive. In particular all the variants and embodiments described previously can be combined with each other.

For example, a production process according to the invention can comprise the "release" of the electrodes (production of the holes 21), the production of the antenna 14, the holes 21 and the antenna 14 not being incompatible.

The invention claimed is:

1. Process for producing a piezoelectric sensor (1), comprising the following steps:
   producing, on a support (10), a stack of sensor layers (2, 4, 5, 12, 19), the sensor layers comprising a layer of piezoelectric material (5) comprised between a first electrode (6, 7) and a second electrode (8, 9), the first electrode not being in contact with the second electrode, the stack of sensor layers comprising a first conductive layer (2), and a second conductive layer (4), each of the first (2) and second (4) conductive layers comprising two parts, a first part (6) of the first conductive layer being in contact with a first part (7) of the second conductive layer, a second part (8) of the first conductive layer being in contact with a second part (9) of the second conductive layer, the first electrode (6, 7) being formed by the first part of the first conductive layer and by the first part of the second conductive layer, the second electrode (8, 9) being formed by the second part of the first conductive layer and by the second part of the second conductive layer, the layer of piezoelectric material (5) being comprised at least in part between the first conductive layer and the second conductive layer, then
   while the sensor layers (2, 4, 5, 12, 19) are still carried by the support (10), coating the sensor layers with a first layer (11) of polymer, then
   removing at least a part of the support (10) from the stack of sensor layers.

2. Process according to claim 1, wherein, after the removal of the at least a part of the support, a second layer (24) of polymer is produced, so that the sensor layers (2, 4, 5, 12, 19) are encapsulated between the first polymer layer (11) and the second polymer layer (24).

3. Process according to claim 1, wherein all of the support (10) is removed from the stack of sensor layers.

4. Process according to claim 1, wherein the support (10) is a rigid support having, under standard ambient conditions of a temperature of 25° C. and absolute pressure of 0.986 atm., a Young's modulus greater than 100 GPa.

5. Process according to claim 1, which also comprises the production of an antenna linking the first electrode to the second electrode, said antenna making one or more turns so as to create a closed loop.

6. Process according to claim 5, wherein the piezoelectric layer (5) is in the form of a bar extending longitudinally and in that the bar extends longitudinally from the perimeter of the loop and towards the inside of the loop.

7. Process according to claim 5, wherein the sensor layers comprise an insulating layer, produced between the antenna and the first electrode and produced between the antenna and the second electrode, at zones where the antenna is superimposed on the first electrode or the second electrode.

8. Process according to claim 7, wherein the insulating layer is produced from an electrically insulating material, having an electrical resistivity greater than $10^3$ ohm·cm under standard ambient conditions of a temperature of 25° C. and absolute pressure of 0.986 atm.

9. Process according to claim 7, wherein the sensor layers also comprise a stiffening layer (12) superimposed on the piezoelectric layer.

10. Process according to claim 9, wherein in the stiffening layer and the insulating layer are produced from one and the same material during one and the same layer deposition step.

11. Process according to claim 1, wherein the total thickness of the sensor layers (2, 4, 5, 12, 19) is less than 3 micrometers.

12. Sensor (1) obtained by a production process according to claim 1.

13. Process for using a sensor obtained according to claim 1, comprises the following steps:
   the sensor (1) is applied on a human or animal body, then
   for each heartbeat of said body among several beats, the heartbeat deforms the piezoelectric layer (5), generating a variation in electric charge in the electrodes (6, 7; 8, 9),
   for each variation in electric charge, this variation in electric charge is detected, and
   a heart rate of the body is deduced from these detections.

14. Process for using a sensor obtained according to claim 1, which comprises the following steps:
   the sensor is applied on a human or animal body, then
   an electromagnetic field is emitted by excitation electronics, then
   the electromagnetic field is picked up by an antenna electrically connected to the first electrode (6, 7) and to the second (8, 9) electrode of the sensor (1), generating an electric current in the antenna, at a frequency f1 equal to a resonance frequency f0 of the inactive sensor or to a harmonic of this resonance frequency f0,
   for each heartbeat of said body among several beats, the heartbeat deforms the piezoelectric layer (5), causing a variation Df in the resonance frequency,
   for each variation Df in the resonance frequency, a signal oscillating at a frequency f1+Df is received by measurement electronics,
   a heart rate of the body is deduced from these detections.

15. Process according to claim 1, wherein the sensor layers also comprise a stiffening layer (12) superimposed on the piezoelectric layer.

16. Process according to claim 8, wherein the stiffening layer and the insulating layer are produced from one and the same material during one and the same layer deposition step.

* * * * *